(12) United States Patent
Terashima et al.

(10) Patent No.: US 7,115,195 B2
(45) Date of Patent: Oct. 3, 2006

(54) ION SELECTIVE MONOELECTRODE COMPLEX

(75) Inventors: Masaaki Terashima, Saitama (JP); Osamu Seshimoto, Saitama (JP)

(73) Assignee: Fuji Photo Film Co., Ltd., Saitama (JP)

( * ) Notice: Subject to any disclaimer, the term of this patent is extended or adjusted under 35 U.S.C. 154(b) by 0 days.

(21) Appl. No.: 10/856,650

(22) Filed: May 27, 2004

(65) Prior Publication Data

US 2004/0216999 A1    Nov. 4, 2004

Related U.S. Application Data

(62) Division of application No. 09/981,528, filed on Oct. 17, 2001, now Pat. No. 6,767,578.

(30) Foreign Application Priority Data

Oct. 17, 2000    (JP) .............................. 2000-316977

(51) Int. Cl.
*G01N 27/333*    (2006.01)

(52) U.S. Cl. ...................................... 204/418; 204/416
(58) Field of Classification Search ......... 204/416–418
See application file for complete search history.

(56) References Cited

U.S. PATENT DOCUMENTS 4,684,445 A  *  8/1987  Seshimoto et al. .......... 205/789

* cited by examiner

*Primary Examiner*—Alex Noguerola
(74) *Attorney, Agent, or Firm*—Reed Smith LLP

(57) ABSTRACT

An ion selective monoelectrode complex which is favorably employable to manufacture an ion activity measuring apparatus, has on a common non-electroconductive support sheet, plural ion selective monoelectrodes each of which is composed of an electrode composite consisting of, in order, a silver metal layer, a silver halide layer, an electrolytic material layer, and an ion selective membrane, and an electroconductive terminal which is electrically connected to the silver metal layer and which has an exposed surface, under the condition that the ion selective monoelectrodes are aligned, without electric contact with each other, along an imaginary line bridging the electrode composite and the electroconductive terminal.

9 Claims, 8 Drawing Sheets

ION SELECTIVE MONOELECTRODE COMPLEX

CROSS-REFERENCES TO RELATED APPLICATIONS

This application is a divisional of U.S. patent application Ser. No. 09/981,528 filed Oct. 17, 2001 now U.S. Pat. No. 6,767,578 which claims priority of Japanese Application No. 2000-316977 filed Oct. 17, 2000, the complete disclosures of which are hereby incorporated by reference.

FIELD OF THE INVENTION

The present invention relates to an ion selective monoelectrode complex and an ionic activity-measuring apparatus which is favorably employable for analysis of ionic components in liquid samples such as a whole blood sample, a serum sample, and a urine sample.

BACKGROUND OF THE INVENTION

An ionic activity-measuring apparatus utilizing an ion selective electrode is widely employed for analyzing ionic components in a liquid sample such as a whole blood sample or a serum sample.

U.S. Pat. No. 4,571,293 (which corresponds to EP 0 160 997 B1) discloses an ionic activity-measuring apparatus using an ion selective electrode which is illustrated in FIG. 1 of the drawings attached to this specification.

In FIG. 1, the ionic activity-measuring apparatus comprises a non-electroconductive support 11, a pair of electrodes each of which comprises a silver metal layer 12a, 12b and a silver halide layer 13a, 13b, a common electrolytic material layer 14, a common ion selective membrane 15, and a common non-electroconductive cover sheet 16 having a pair of openings 17a, 17b for receiving and keeping a sample solution and a reference solution, respectively, each opening being placed above each electrode unit, and having thereon an a bridge member 18 for electrically bridging the sample solution received in one opening 17a and the reference solution received in another opening 17b. Each of the silver metal layer 12a, 12b has an exposed surface 10a, 10b, respectively. By placing probes of a potentiometer 19 on these exposed silver metal surface 10a, 10b, the produced electric potential difference can be measured.

FIG. 2 illustrates an industrially employed process for preparing the ionic activity-measuring apparatus of FIG. 1.

In industry, the ionic activity-measuring apparatus of FIG. 1 is generally manufactured in a mass scale, by the steps of:

(1) preparing a longitudinal sheet composed of a non-electroconductive sheet 11 and a silver metal layer 12 deposited or laminated on the non-electroconductive sheet 11;

(2) making a linear scratch 21 on the silver metal layer 12 under the condition that the scratch is extended in the longitudinal direction and reach the non-electro-conductive sheet 11, to divide the silver metal layer 12 into two silver metal portions 12a, 12b, and covering each silver metal portion 12a, 12b on its side areas with a polymer material layer 20a, 20b, leaving uncovered area in the form of a stripe (or belt) on the silver metal portion 12a, 12b;

(3) halogenating the silver metal portion 12a, 12b in the uncovered areas to form silver halide layers 13a, 13b, respectively, on the surface of the silver metal portion in the uncovered area;

(4) forming an electrolytic material layer 14 on the scratch and the silver halide portions;

(5) peeling the polymer material layer 20a, 20b off from the silver metal layer to produce an exposed silver metal area 10a, 10b, and placing an ion selective membrane 15 on an electrolytic material layer 14; and (6) finally placing a non-electroconductive member 16 having two openings 17a, 17b on the ion selective membrane 15 and then placing a bridge 18 on the member 16 to connect the openings 12a, 17b.

The above-described industrial method is advantageous for manufacturing a great number of ion selective electrodes in a mass scale.

The ion selective electrode can measure an ionic activity of $H^+$, $Li^+$, $Na^+$, $K_+$, $Mg^{2+}$, $Ca^{2+}$, $Cl^-$, $HCO_3^{31}$ , or $CO_3^{2-}$, by employing an appropriate ion selective membrane.

U.S. Pat. No. 4,789,435 describes an ion selective electrode assembly comprising plural ion selective electrodes for analyzing plural ionic components such as $Na^+$, $K^+$, and $Cl^-$, simultaneously. In the assembly, one of plural ion selective electrodes has an ion selective membrane differing from that of other ion selective electrode in chemical composition.

SUMMARY OF THE INVENTION

It is an object of the present invention to provide an ion selective electrode having a satisfactory analytical performance at a relatively low production cost.

The object of the invention also resides in providing a method of manufacturing ion selective electrodes having satisfactory analytical performance in a mass scale at a relatively low production cost.

The present invention resides in an ion selective monoelectrode complex (hereinafter referred to as "Type A" complex), on a common non-electroconductive support sheet, plural ion selective monoelectrodes each of which is composed of an electrode composite comprising, in order, a silver metal layer, a silver halide layer, an electrolytic material layer, and an ion selective membrane, and an electroconductive terminal which is electrically connected to the silver metal layer and which has an exposed surface, under the condition that the ion selective monoelectrodes are aligned, without electric contact with each other, along an imaginary line bridging the electrode composite and the electroconductive terminal The above-mentioned ion selective electrode of Type A is preferably manufactured in a mass scale by a process comprising the steps of:

making two or more linear scratches on a longitudinal non-electroconductive sheet having thereon a silver metal layer under the condition that the scratches are extended in the longitudinal direction and reach the non-electroconductive sheet;

covering the silver metal layer with a polymer material layer in the form of a stripe on one side of each linear scratch, leaving uncovered area in the form of a stripe;

halogenating the silver metal layer in the uncovered area to form a silver halide layer on the surface of the silver metal layer in the uncovered area;

forming an electrolytic material layer on the polymer material layer and the silver halide layer;

peeling the polymer material layer off from the silver metal layer to remove the polymer material layer and the electrolytic material layer placed on the polymer material layer simultaneously;

placing an ion selective membrane on an electrolytic material layer formed on the silver halide layer; and cutting thus processed longitudinal sheet in the direction traversing the longitudinal sheet to give a plurality of the ion selective monoelectrode complexes.

The ion selective electrode of Type A is also preferably manufactured in a mass scale by a process comprising the steps of:

covering a longitudinal non-electroconductive sheet having thereon a silver metal layer with two or more polymer material layers in the form of a stripe in the longitudinal direction, leaving uncovered area in the form of a stripe;

making one or more linear scratches on the silver metal layer in the vicinity of the polymer material layers under the condition that the scratches are extended in the longitudinal direction and reach the non-electroconductive sheet;

halogenating the silver metal layer in the uncovered area to form a silver halide layer on the surface of the silver metal layer in the uncovered area;

forming an electrolytic material layer on the polymer material layer and the silver halide layer;

peeling the polymer material layer off from the silver metal layer to remove the polymer material layer and the electrolytic material layer placed on the polymer material layer, simultaneously;

placing an ion selective membrane on an electrolytic material layer formed on the silver halide layer; and cutting thus processed longitudinal sheet in the direction traversing the longitudinal sheet to give a plurality of the ion selective monoelectrode complexes.

The present invention also resides in an ionic activity measuring apparatus (of Type A) comprising a pair of the ion selective monoelectrode complex, which are arranged in parallel without electric contact with each other, a non-electroconductive covering element having openings which is placed on the ion selective membranes of the complexes to receive and keep an applied liquid sample to bring it into contact with an ion selective membrane of each ion selective monoelectrode, and bridge elements placed on the covering element to connect one opening placed on an ion selective membrane of one ion selective monoelectrode complex with other opening placed on an ion selective membrane of another ion selective monoelectrode complex.

The invention further resides in an ion selective monoelectrode complex (hereinafter referred to as "Type B" complex), having, on a common non-electroconductive support sheet, plural ion selective monoelectrodes each of which is composed of an electrode composite comprising, in order, a silver metal layer, a silver halide layer, an electrolytic material layer, and an ion selective membrane, all silver metal layers being electrically connected with each other, and an electroconductive terminal which is electrically connected to one of the silver metal layers and which has an exposed surface, under the condition that the ion selective monoelectrodes are aligned along an imaginary line bridging the electrode composite and the electroconductive terminal.

The above-mentioned ion selective electrode (of Type B) of the invention is preferably manufactured in a mass scale by a process comprising the steps of:

covering a silver metal layer placed on a longitudinal non-electroconductive sheet with a polymer material layer in the form of a stripe on a side of the sheet, leaving uncovered area in the form of a stripe;

halogenating the silver metal layer in the uncovered area to form a silver halide layer on the surface of the silver metal layer in the uncovered area;

forming an electrolytic material layer on the polymer material layer and the silver halide layer;

peeling the polymer material layer off from the silver metal layer to remove the polymer material layer and the electrolytic material layer placed on the polymer material layer, simultaneously;

placing an ion selective membrane on an electrolytic material layer formed on the silver halide layer; and cutting thus processed longitudinal sheet in the direction traversing the longitudinal sheet to give a plurality of the ion selective monoelectrode complexes.

The invention furthermore resides in an ionic activity measuring apparatus (of Type B) comprising a pair of the ion selective monoelectrode complex, which are arranged in parallel without electric contact with each other, a non-electroconductive covering element having openings which is placed on the ion selective membranes of the complexes to receive and keep an applied liquid sample to bring it into contact with an ion selective membrane of each ion selective monoelectrode, and bridge elements placed on the covering element to connect one opening placed on an ion selective membrane of one ion selective monoelectrode complex with other opening placed on an ion selective membrane of another ion selective monoelectrode complex.

DETAILED DESCRIPTION OF THE INVENTION

The present invention is further described by referring to the figures illustrated in the attached drawings. The ion selective monoelectrode complex of the invention and the ionic activity-measuring apparatus of the invention is classified into two types, that is, Type A and Type B. Both monoelectrode complexes and apparatuses are described below in order.

[Type A]

Figure 1:
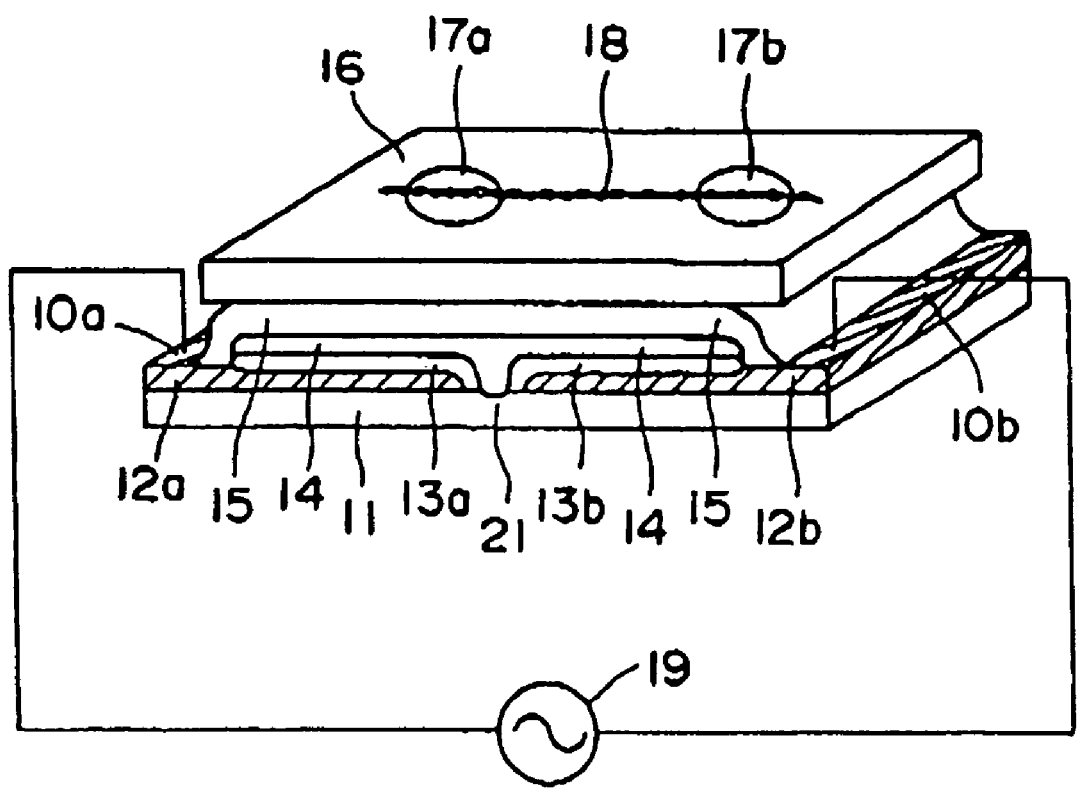
FIG. 1 illustrates a representative structure of a conventional ionic activity-measuring apparatus.
Figure 2:
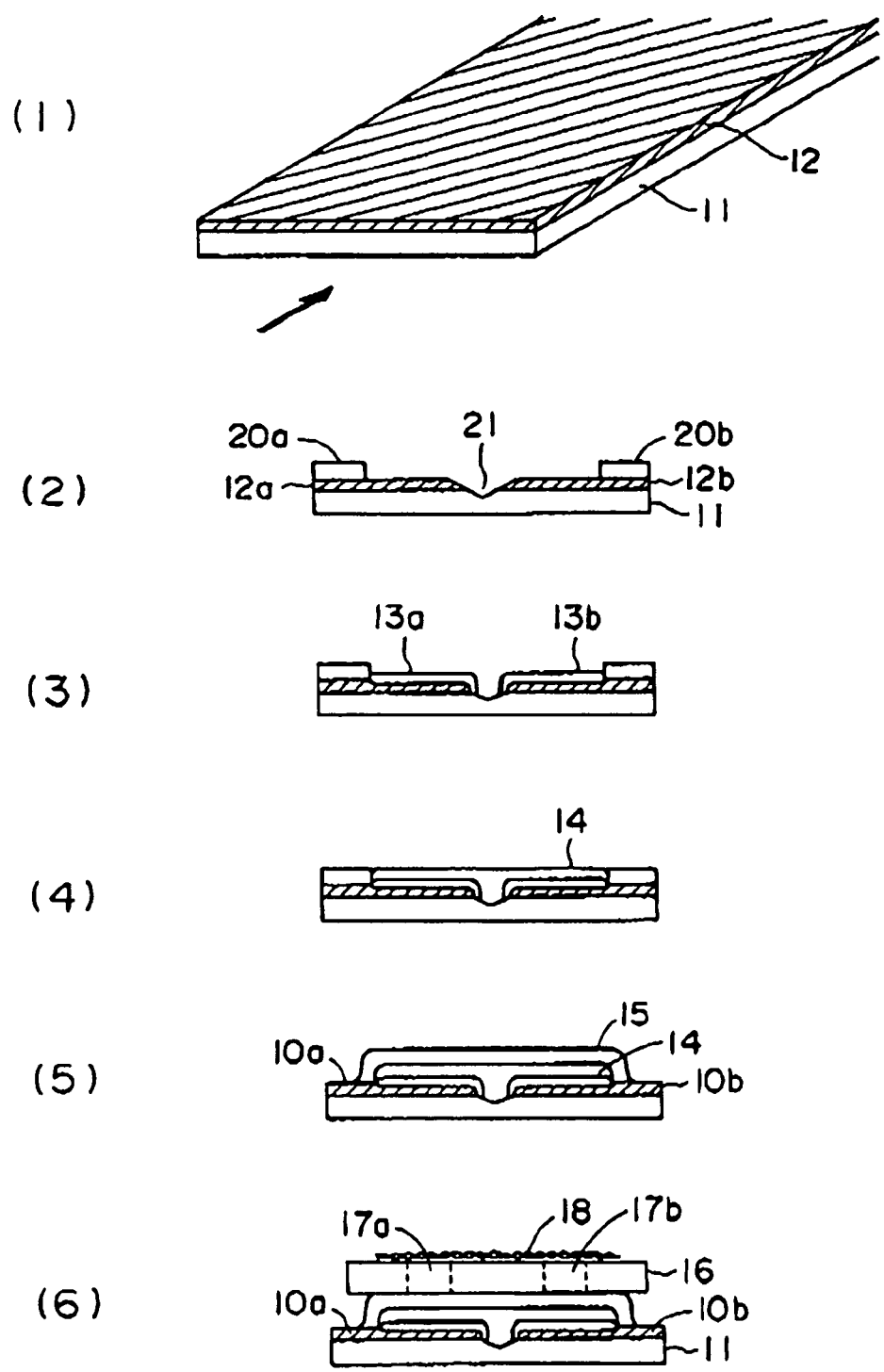
FIG. 2 illustrates a representative process for the preparation of the ionic activity-measuring apparatus of FIG. 1.
Figure 3:
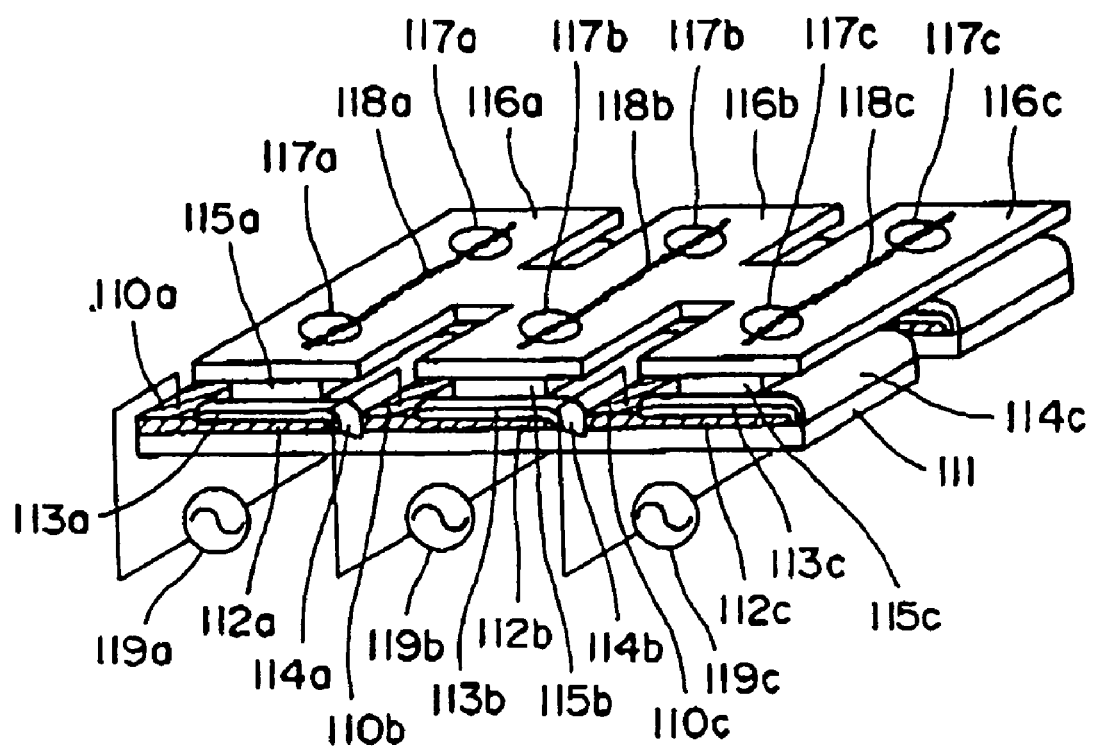
FIG. 3 illustrates a representative structure of an ionic activity-measuring apparatus (of Type A) according to the invention.

FIG. 3 illustrates a representative structure of an ionic activity-measuring apparatus (of Type A) according to the invention.

The ionic activity-measuring apparatus of FIG. 3 can measure three different ionic species such as sodium ion ($Na^+$), potassium ion ($K^+$), and chloride ion ($Cl^-$), almost simultaneously.

The ionic activity-measuring apparatus of Type A in FIG. 3 is composed of an ion selective monoelectrode complex of Type A which has, on a common non-electroconductive support sheet 111, three ion selective mono-electrodes (for the measurements of $Na^+$, $K^+$, and $Cl^-$), each of which is composed of an electrode composite comprising, in order, a silver metal layer 112a, 112b, 112c, a silver halide layer 113a, 113b, 113c, an electrolytic material layer 114a, 114b, 114c, and an ion selective membrane 115a, 115b, 115c, and an electroconductive terminal having an exposed surface 110a, 110b, 110c, which is electrically connected to the silver metal layer 112a, 112b, 112c, respectively. The materials of the ion selective membranes 115a, 115b, 115c are different from each other so that a sodium ion selective monoelectrode, a potassium ion selective monoelectrode, and a chloride ion selective monoelectrode can be produced.

The ion selective monoelectrodes are aligned, with-out electric contact with each other by the scratch formed on the non-electroconductive support sheet 111, along an imaginary line bridging the electrode composite and the electroconductive terminal, that is, the alignment of terminal 110a—silver metal layer 112a—terminal 110b—silver metal layer 112b—terminal 110c—silver metal layer 112c. In the scratches, an electrolytic material extending from the adjacent electrolytic material layer is embedded.

The ionic activity-measuring apparatus is composed of a pair of the ion selective monoelectrode complex which are arranged in parallel.

On each of a pair of the sodium ion selective monoelectrodes, a pair of the potassium ion selective monoelectrodes, and a pair of the chloride ion selective monoelectrodes are placed a non-electroconductive plate unit 116a, 116b, 116c having a pair of openings 117a, 117b, 117c for receiving and holding a sample solution and a reference solution. In FIG. 3, three non-electroconductive plate units are combined to produce one plate.

On the non-electroconductive plate unit 116a, 116b, 116c are placed a bridge member 118a, 118b, 118c, which can bridge electrically a sample solution received in one opening and a reference solution received in another opening.

Thus, an ionic activity-measuring apparatus of Type A which is a measuring apparatus assembly for measuring sodium ion, potassium ion, and chloride ion, at the same time or different times. In the measurement, an electric conductive probes of a potentiometer 119a, 119b, 119c are brought into contact with the electroconductive terminal 110a, 110b, 110c of the apparatus, and an electric potential difference produced in a measuring apparatus unit which has received a sample solution and a reference solution is measured.

Thus, the ionic activity-measuring apparatus of the invention is characteristic in assembling a pair of ion selective monoelectrode complexes, which is in contrast to the known multiple ionic activity-measuring apparatus which is manufactured by assembling two or more ion selective electrode units having a specific ion selective membrane.

Figure 4:
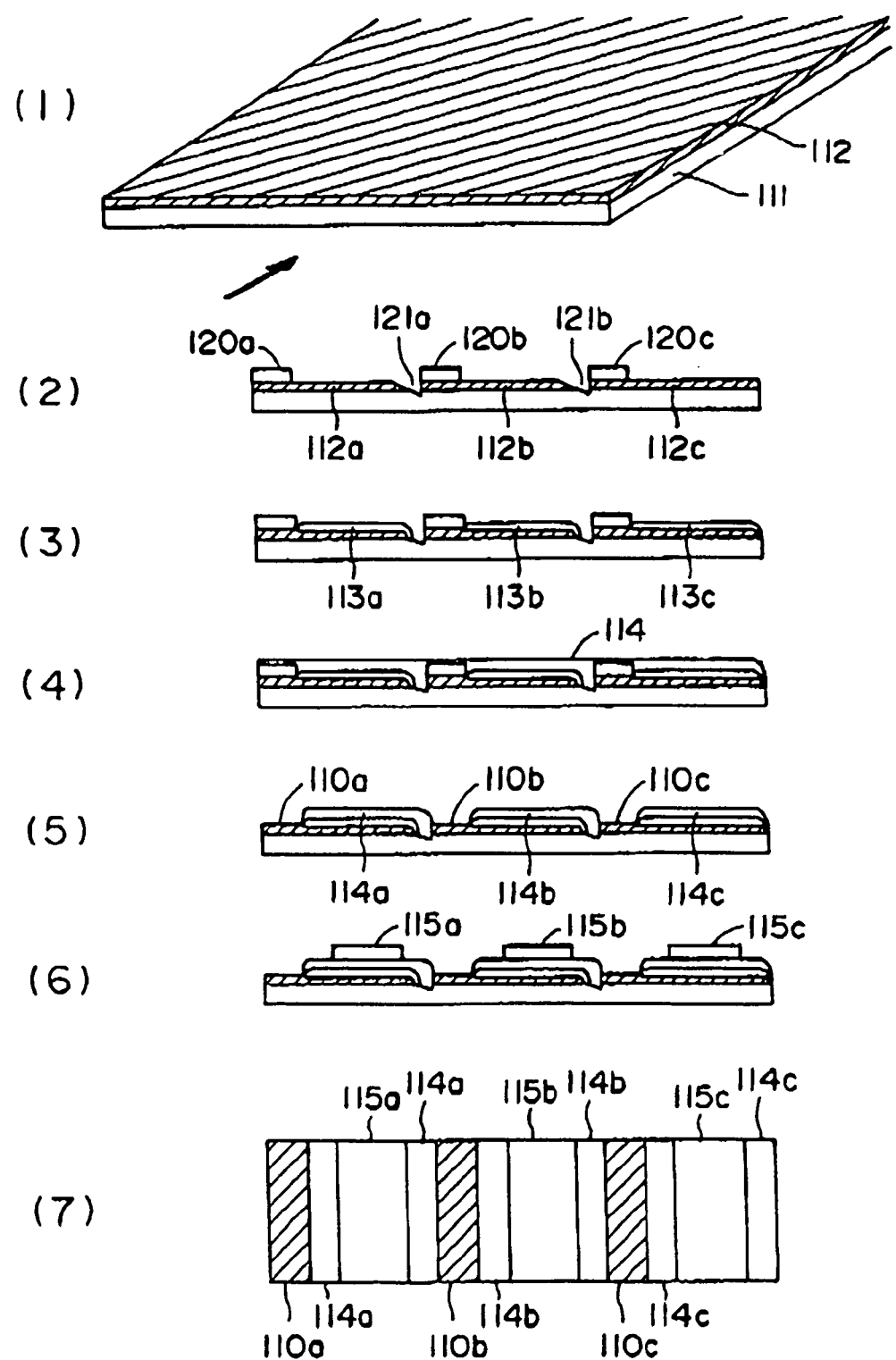
FIG. 4 illustrates a representative process for preparing an ion selective monoelectrode complex (of Type A) of the invention.

FIG. 4 illustrates a representative process for the preparation of a large number of ion selective monoelectrode complexes of Type A, such as those utilized for manufacturing the ionic activity-measuring apparatus of FIG. 3.

The process comprises the following steps:

(1) preparing a longitudinal (or continuous) non-electroconductive sheet 111 having a silver metal layer 112 on its surface;

(2) producing two linear scratches 121a, 121b on the silver metal layer 112, under the condition that the scratches 121a, 121b are extended in the longitudinal direction and reach the surface of the non-electroconductive sheet 111 to divide the silver metal layer 112 into three silver metal layers 112a, 112b, 112c, and covering each of the divided silver metal layers 112a, 112b, 112c with a polymer material layer in the form of a stripe 120a, 120b, 120c, on one side of each linear scratch and on the side of the non-electroconductive sheet 111, leaving uncovered area in the form of a stripe;

(3) halogenating the silver metal layer 112a, 112b, 112c in the uncovered area to form a silver halide layer 113a, 113b, 113c on the surface of the silver metal layer in the uncovered area;

(4) forming an electrolytic material layer 114 on the polymer material layer 120a, 120b, 120c and the silver halide layer 113a, 113b, 113c;

(5) peeling the polymer material layer 120a, 120b, 120c off from the silver metal layer to remove the polymer material layer and the electrolytic material layer placed on the polymer material layer simultaneously, to divide the electrolytic material layer to three electrolytic material layers 114a, 114b, 114c and produce exposed areas 110a, 110b, 110c on the silver metal layers 112a, 112b, 112c;

(6) placing an ion selective membrane 115a, 115b, 115c on the electrolytic material layer 114a, 114b, 114c; and (7) cutting thus processed longitudinal sheet in the direction traversing the longitudinal sheet to give a plurality of the ion selective monoelectrode complexes having the illustrated pattern (plane view).

The halogenation of the silver metal layer in the step (3) can be carried out in the known manner such as that employing an aqueous dichromate solution or an aqueous PDTA•Fe(III) solution. Otherwise, a dispersion containing silver halide particles and a binder can be coated on the silver metal layer and dried to form a silver halide layer. In the step (4), the electrolytic material layer can be independently formed on each silver halide layer, so that an electrolytic material suitable for each ion selective membrane to be coated on the electrolytic material layer can be selected.

For the producing the ion selective monoelectrode complex and manufacturing the ionic activity-measuring apparatus, a variety of known materials and technologies can be adopted. Examples of these known materials and technologies are described in U.S. Pat. No. 4,053,381, No. 4,171,246, and No. 4,214,968, and Research Disclosure No. 16113 (September, 1977).

Figure 5:
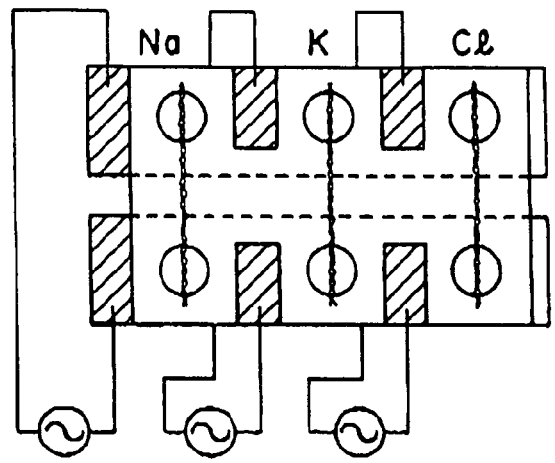
FIG. 5 illustrates an example of possible arrangement of two ion selective monoelectrode complexes for manufacturing an ionic activity-measuring apparatus (of Type A) of the invention.

FIG. 5 is a plane view of the arrangement of the ionic activity-measuring apparatus of FIG. 3.

Figure 6:
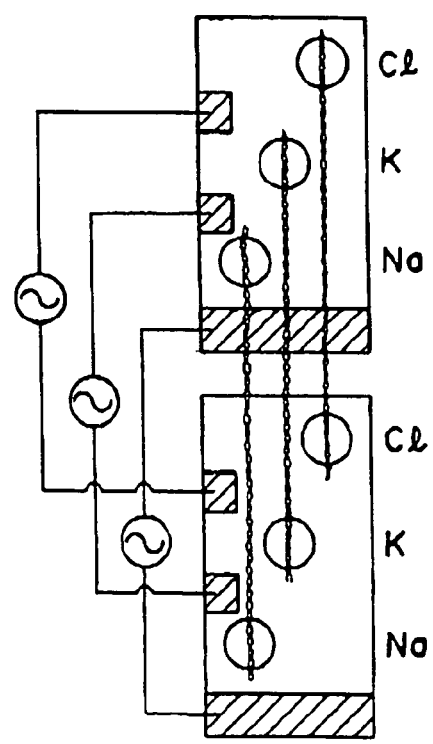
FIG. 6 illustrates another example of possible arrangement of two ion selective monoelectrode complexes for manufacturing an ionic activity-measuring apparatus (of Type A) of the invention.

Alternatively, a pair of the ion selective monoelectrode complexes can be arranged in the manner illustrated in FIG. 6.

[Type B]

Figure 7:
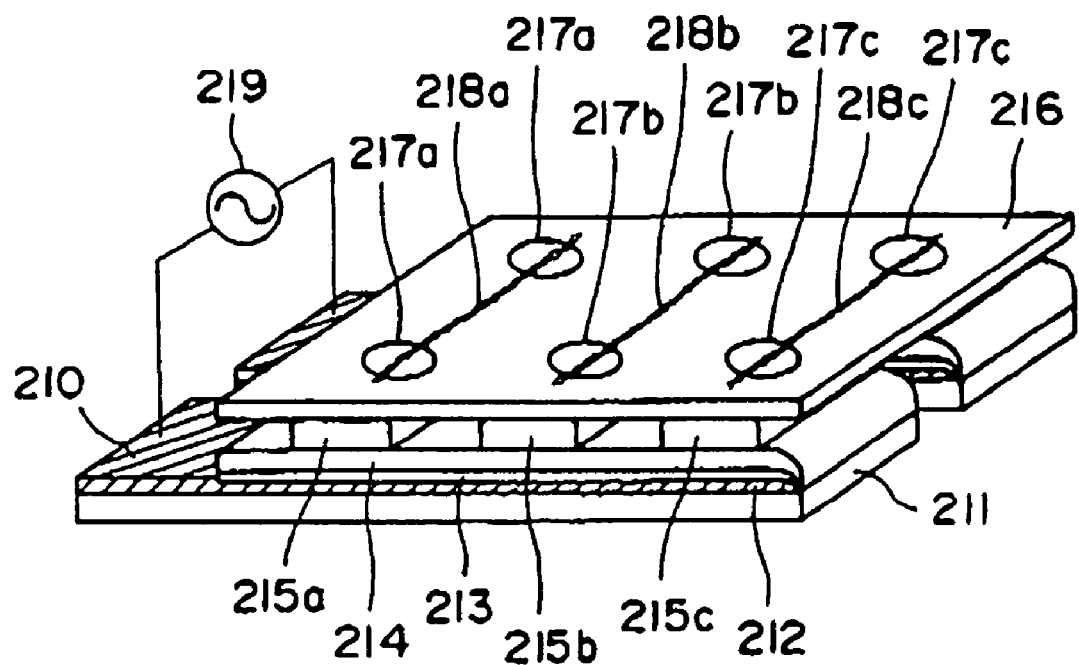
FIG. 7 illustrates a representative structure of an ionic activity-measuring apparatus (of Type B) according to the invention.

FIG. 7 illustrates a representative structure of an ionic activity-measuring apparatus (of Type B) according to the invention.

The ionic activity-measuring apparatus of FIG. 7 can measure three different ionic species such as sodium ion ($Na^+$), potassium ion ($K^+$), and chloride ion ($Cl^-$), almost simultaneously.

The ionic activity-measuring apparatus of Type B in FIG. 7 is composed of an ion selective monoelectrode complex of Type B which has, on a common non-electroconductive support sheet 211, three ion selective monoelectrodes electrodes (for the measurements of $Na^+$, $K^+$, and $Cl^-$), each of which is composed of an electrode composite comprising, in order, a common silver metal layer 212, a common silver halide layer 213, a common electrolytic material layer 214, and an ion selective membrane 215a, 215b, 215c, and an electroconductive terminal having an exposed surface 210, which is electrically connected to the silver metal layer 212. The materials of the ion selective membranes 215a, 215b, 215c are different from each other so that a sodium ion selective monoelectrode, a potassium ion selective monoelectrode, and a chloride ion selective monoelectrode can be produced.

The ion selective monoelectrodes are aligned along an imaginary line bridging the electrode composite and the electroconductive terminal, that is, the alignment of terminal 210—ion selective membrane 215a—ion selective membrane 215b—ion selective membrane 215c.

The ionic activity-measuring apparatus is composed of a pair of the ion selective monoelectrode complex which are arranged in parallel.

On each of a pair of the sodium ion selective monoelectrodes, a pair of the potassium ion selective monoelectrodes, and a pair of the chloride ion selective monoelectrodes are placed a non-electroconductive plate 216 having three pairs of openings 217a, 217b, 217c for receiving and holding a sample solution and a reference solution. On the non-electroconductive plate unit 216a, 216b, 216c are placed a bridge member 218a, 218b, 218c, which can bridge electrically a sample solution received in one opening and a reference solution received in another opening.

Thus, an ionic activity-measuring apparatus of Type B which is a measuring apparatus assembly for measuring sodium ion, potassium ion, or chloride ion. In the measurement, an electric conductive probes of a potentiometer 219 is brought into contact with the electroconductive terminal 210 of the apparatus, and an electric potential difference produced in a measuring apparatus unit which has received a sample solution and a reference solution is measured.

Figure 8:
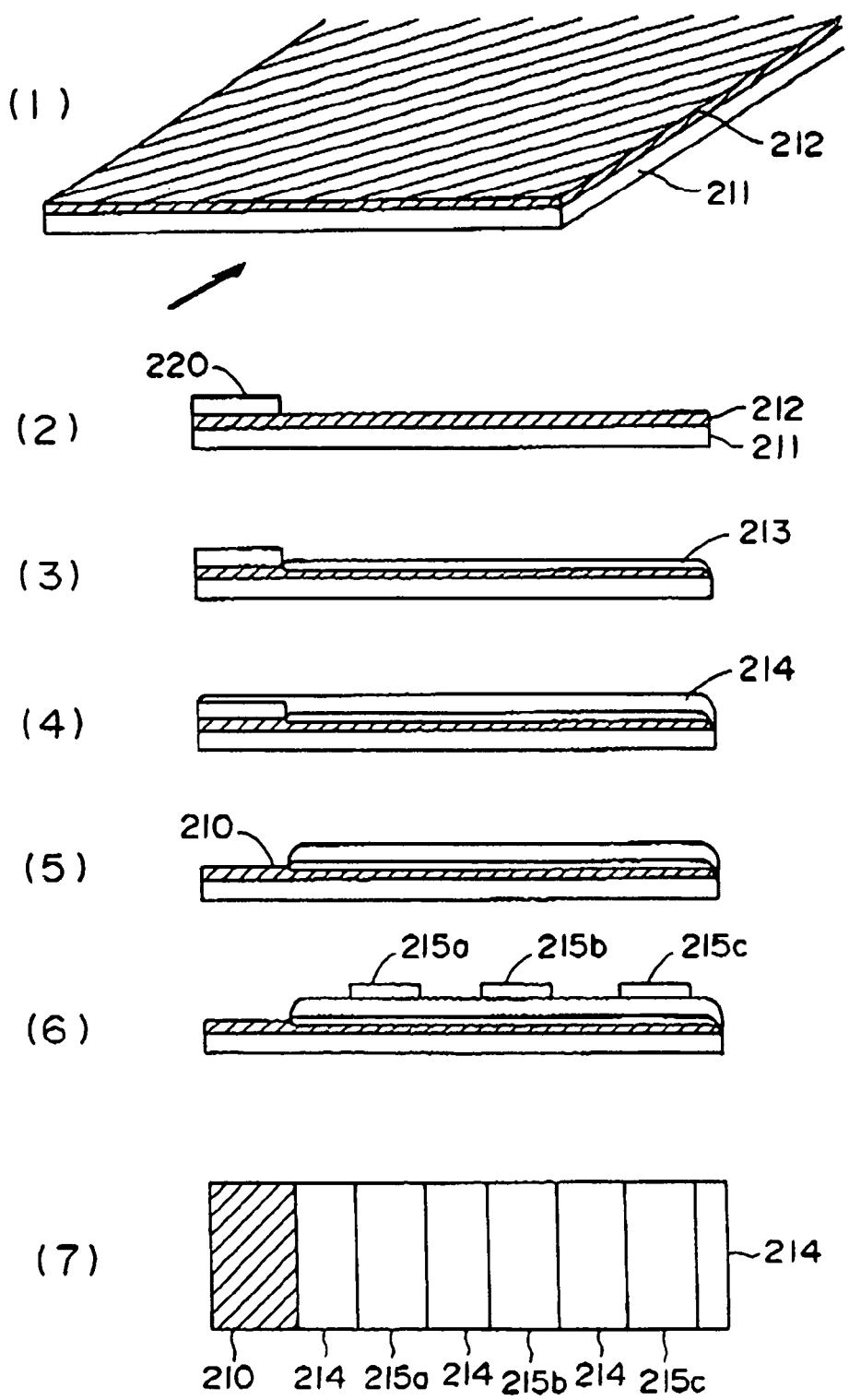
FIG. 8 illustrates a representative process for preparing an ion selective monoelectrode complex (of Type B) of the invention.

FIG. 8 illustrates a representative process for the preparation of a large number of ion selective monoelectrode complexes of Type B, such as those utilized for manufacturing the ionic activity-measuring apparatus of FIG. 7.

The process comprises the following steps:

(1) preparing a longitudinal (or continuous) non-electroconductive sheet 211 having a silver metal layer 212 on its surface;

(2) covering a silver metal layer 212 with a polymer material layer 220 in the form of a stripe on a side of the sheet, leaving uncovered area in the form of a stripe;

(3) halogenating the surface of the silver metal layer 212 in the uncovered area to form a silver halide layer 213 on the surface of the silver metal layer 212 in the uncovered area;

(4) forming an electrolytic material layer 214 on the polymer material layer 220 and the silver halide layer 213;

(5) peeling the polymer material layer 220 off from the silver metal layer 212 to remove the polymer material layer 220 and the electrolytic material layer placed on the polymer material layer, simultaneously;

(6) placing three ion selective membranes 215a, 215b, 215c on the electrolytic material layer 214; and (7) cutting thus processed longitudinal sheet in the direction traversing the longitudinal sheet to give a plurality of the ion selective monoelectrode complexes having the illustrated pattern (plane view).

Figure 9:
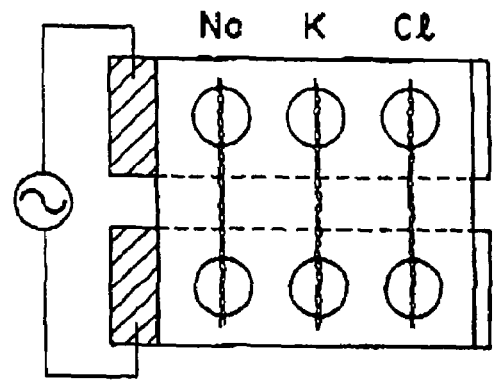
FIG. 9 illustrates an example of possible arrangement of two ion selective monoelectrode complexes for manufacturing an ionic activity-measuring apparatus (of Type B) of the invention.

FIG. 9 is a plane view of the arrangement of the ionic activity-measuring apparatus of FIG. 7.

Figure 10:
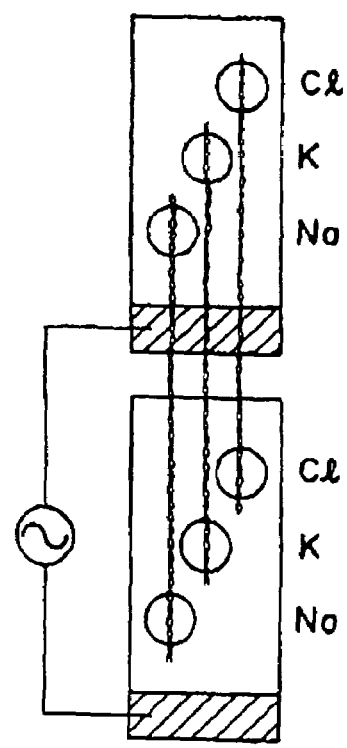
FIG. 10 illustrates another example of possible arrangement of two ion selective monoelectrode complexes for manufacturing an ionic activity-measuring apparatus (of Type B) of the invention.

Alternatively, a pair of the ion selective monoelectrode complexes can be arranged in the manner illustrated in FIG. 10.

The ion selective monoelectrode complexes of Type A or Type B can be placed inversely and assembled to constitute an ionic activity-measuring apparatus illustrated in U.S. Pat. No. 4,789,435.

The present invention is further described in the following examples.

EXAMPLE 1

On a longitudinal polyethylene terephthalate film (support, thickness 180 μm, length 300 m, width 1300 mm) was deposited a silver metal layer (thickness approx. 8,000 angstroms) by continuous vacuum deposition. The film was slitted in the longitudinal direction to give a continuous silver metal-coated strip having a width of 24 mm.

On the silver metal layer were placed three film forming polymer material layers (thickness: 30 μm, produced using vinyl chloride-vinyl acetate copolymer in a mixture of toluene and methyl ethyl ketone) in the form of stripes (width: 4 mm, space between the stripes: 4 mm). A scratch or groove (depth of 70 μm) was produced on the silver metal layer and support on the left side of each polymer material layer, to give three divided silver metal layers.

Thus treated longitudinal film was then placed in an aqueous oxidation-halogenation processing solution containing 60 mM of hydrochloric acid and 12 mM of potassium dichromate for 90 seconds, for performing catalytic oxidation-chlorination processing. The processed film was recovered, washed with water, and dried to give a film having on its surface plural Ag/AgCl electrode composites.

A solution of electrolytic material was prepared by dissolving 2.975 g of sodium chloride in 42.5 g of an aqueous organic solvent mixture of 2.5 g of acetone, 20 g of ethanol, and 20 g of water. The solution was then coated on the Ag/AgCl electrode composites and dried to give an electrolytic material layer in an amount of 2.2 g/m².

The polymer films were peeled off from the silver metal layer, to remove simultaneously the electrolytic material placed on the polymer films. Thus portions of the silver metal layer were exposed.

Separately, the following three coating solutions of ion selective membrane materials were prepared:

(1) Composition of sodium ion selective membrane-forming solution

| | |
|---|---|
| Vinyl chloride-vinyl acetate copolymer (VYNS, available from Union carbide) | 0.9 g |
| Phenyl dicresyl phosphate | 1.2 g |
| Methylmonensin | 0.1 g |
| Sodium tetraphenylborate | 2 mg |
| Methyl ethyl ketone | 4 g |

(2) Composition of potassium ion selective membrane-forming solution

-continued

| | |
|---|---|
| VYNS | 0.9 g |
| Dioctyl adipate | 1.2 g |
| Valinomycin | 44 mg |
| Potassium tetrakis-p-chlorophenylborate | 18 mg |
| Methyl ethyl ketone | 5 g |
| 1% SH510 (polysiloxane in methyl ethyl ketone) | 50 mg |
| (3) Composition of chloride ion selective membrane-forming solution | |
| VYNS | 0.9 g |
| Capricoat | 1.3 g |
| Didodecyl phthalate | 0.05 g |
| Ammonium trioctylpropylchloride | 0.05 g |

Each of the compositions were continuously spread on each electrolytic material layer sin the form of stripe of the longitudinal film moving at a rate of 15 m/min., to give three stripes of ion selective layer (width 4 mm).

The longitudinal film was cut in the width direction at a distance of 4 mm to give plural ion selective monoelectrode complexes (24 mm×4 mm).

A pair of thus produced ion selective monoelectrode complexes were assembled to constitute an ionic activity-measuring apparatus for the ionic analysis of Na, K and Cl, in the form illustrated in FIG. 3.

What is claimed is:

1. An ion selective monoelectrode complex having, on a common non-electroconductive support sheet, plural ion selective monoelectrodes each of which is composed of an electrode composite comprising, in order, a silver metal layer, a silver halide layer, an electrolytic material layer, and an ion selective membrane, and an electroconductive terminal which is electrically connected to the silver metal layer and which has an exposed surface, under the condition that the ion selective monoelectrodes are aligned, without electric contact with each other, along an imaginary line bridging the electrode composite and the electroconductive terminal and under the further condition that at least one electroconductive terminal is arranged between adjoining ion selective monoelectrodes.

2. The ion selective monoelectrode complex of claim 1, wherein one ion selective monoelectrode has an ion selective membrane which is responsive to one ionic species, while other one or more ion selective monoelectrodes have an ion selective membrane which is responsive to other ionic species.

3. The ion selective monoelectrode complex of claim 1, which comprises three or more ion selective monoelectrodes that are aligned without electric contact with each other, along an imaginary line bridging the electrode composite and the electroconductive terminal.

4. The ion selective monoelectrode complex of claim 1, wherein the ion selective monoelectrodes are insulated from each other with an electrolytic material extending from the electrolytic material layer of the monoelectrode on one side.

5. An ionic activity measuring apparatus comprising a pair of ion selective monoelectrode complex of claim 1, which are arranged in parallel without electric contact with each other, a non-electroconductive covering element having openings which is placed on the ion selective membranes of the complexes to receive and keep an applied liquid sample to bring it into contact with an ion selective membrane of each ion selective monoelectrode, and bridge elements placed on the covering element to connect one opening placed on an ion selective membrane of one ion selective monoelectrode complex with other opening placed on an ion selective membrane of another ion selective monoelectrode complex.

6. An ion selective monoelectrode complex having, on a common non-electroconductive support sheet, plural ion selective monoelectrodes each of which is composed of an electrode composite comprising, in order, a silver metal layer, a silver halide layer, an electrolytic material layer, and an ion selective membrane, all silver metal layers being electrically connected with each other, and an electroconductive terminal which is electrically connected to one of the silver metal layers and which has an exposed surface, under the condition that the ion selective monoelectrodes are aligned alone an imaginary line bridging the electrode composite and the electroconductive terminal.

7. The ion selective monoelectrode complex of claim 6, wherein one ion selective monoelectrode has an ion selective membrane which is responsive to one ionic species, while other one or more ion selective monoelectrodes have an ion selective membrane which is responsive to other ionic species.

8. The ion selective monoelectrode complex of claim 6, in which the electroconductive terminal is placed on one end of the monoelectrode complex.

9. An ionic activity measuring apparatus comprising a pair of ion selective monoelectrode complex of claim 6, which are arranged in parallel without electric contact with each other, a non-electroconductive covering element having openings which is placed on the ion selective membranes of the complexes to receive and keep an applied liquid sample to bring it into contact with an ion selective membrane of each ion selective monoelectrode, and bridge elements placed on the covering element to connect one opening placed on an ion selective membrane of one ion selective monoelectrode complex with other opening placed on an ion selective membrane of another ion selective monoelectrode complex.

* * * * *

UNITED STATES PATENT AND TRADEMARK OFFICE
CERTIFICATE OF CORRECTION

PATENT NO.        : 7,115,195 B2  
APPLICATION NO.   : 10/856650  
DATED             : November 22, 2006  
INVENTOR(S)       : Masaaki Terashima et al.

It is certified that error appears in the above-identified patent and that said Letters Patent is hereby corrected as shown below:

On the Title Page item 73   now reads, "Assignee: Fuji Photo Film Co., Ltd., Saitama (JP)" and should read, --Assignee: Fuji Photo Film Co., Ltd., Kanagawa (JP)--.

Signed and Sealed this

Third Day of February, 2009

JOHN DOLL  
*Acting Director of the United States Patent and Trademark Office*

UNITED STATES PATENT AND TRADEMARK OFFICE
CERTIFICATE OF CORRECTION

PATENT NO.        : 7,115,195 B2                                          Page 1 of 1
APPLICATION NO. : 10/856650
DATED             : October 3, 2006
INVENTOR(S)       : Masaaki Terashima et al.

It is certified that error appears in the above-identified patent and that said Letters Patent is hereby corrected as shown below:

On the Title Page item 73    now reads, "Assignee: Fuji Photo Film Co., Ltd., Saitama (JP)" and should read, --Assignee: Fuji Photo Film Co., Ltd., Kanagawa (JP)--.

This certificate supersedes the Certificate of Correction issued February 3, 2009.

Signed and Sealed this

Twenty-fourth Day of February, 2009

JOHN DOLL
*Acting Director of the United States Patent and Trademark Office*